(12) United States Patent
Behnam

(10) Patent No.: US 10,779,561 B2
(45) Date of Patent: *Sep. 22, 2020

(54) RESVERATROL SOLUBILITY

(71) Applicant: AQUANOVA AG, Darmstadt (DE)

(72) Inventor: Dariush Behnam, Rossdorf (DE)

(73) Assignee: AQUANOVA AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/309,603

(22) PCT Filed: Jun. 6, 2017

(86) PCT No.: PCT/EP2017/063673
§ 371 (c)(1),
(2) Date: Dec. 13, 2018

(87) PCT Pub. No.: WO2017/215980
PCT Pub. Date: Dec. 21, 2017

(65) Prior Publication Data
US 2019/0223484 A1    Jul. 25, 2019

(30) Foreign Application Priority Data

Jun. 14, 2016 (EP) .................. PCT/EP2016/063577

(51) Int. Cl.
| *A61K 31/05* | (2006.01) |
| *A61K 9/48* | (2006.01) |
| *A61K 8/33* | (2006.01) |
| *A61K 9/107* | (2006.01) |
| *A61K 9/10* | (2006.01) |
| *A61K 47/26* | (2006.01) |
| *A61K 47/14* | (2017.01) |
| *A61P 1/00* | (2006.01) |
| *A23L 29/10* | (2016.01) |
| *A23L 33/11* | (2016.01) |
| *A23L 33/115* | (2016.01) |
| *A23L 2/52* | (2006.01) |
| *A61K 8/34* | (2006.01) |
| *A61K 8/362* | (2006.01) |
| *A61K 8/49* | (2006.01) |

(52) U.S. Cl.
CPC ................ *A23L 29/10* (2016.08); *A23L 2/52* (2013.01); *A23L 33/11* (2016.08); *A23L 33/115* (2016.08); *A61K 8/347* (2013.01); *A61K 8/362* (2013.01); *A61K 8/4973* (2013.01); *A61K 9/10* (2013.01); *A61K 9/1075* (2013.01); *A61K 9/4858* (2013.01); *A61K 31/05* (2013.01); *A61K 47/14* (2013.01); *A61K 47/26* (2013.01); *A23V 2002/00* (2013.01)

(58) Field of Classification Search
None
See application file for complete search history.

(56) References Cited

U.S. PATENT DOCUMENTS

2016/0081976 A1 * 3/2016 Bromley .............. A61K 31/355
424/456

FOREIGN PATENT DOCUMENTS

| DE | 202009016292 U1 | 4/2011 |
| DE | 202012012130 U1 | 4/2014 |
| KR | 2009-0132357 A | 12/2009 |
| WO | 2007/006497 A2 | 1/2007 |

OTHER PUBLICATIONS

Ahmed et al., "Resveratrol self-emulsifying system increase the uptake by endothelial cells and improves protection against oxidative stress-mediated death", European Journal of Pharmaceutics, 2013, vol. 86, No. 3, pp. 418-426. (Year: 2013).*
Authorized Officer: Nora Linder, International Preliminary Report on Patentability issued in PCT application No. PCT/EP2017/063673 dated Dec. 20, 2018.
Nathan Gray, "Resveratrol could enhance exercise performance", NUTRAingredients.com, "Journal of Physiology", Jun 20, 2012, https://www.nutraingredients.com/Article/2012/06/20/Resveratrol-could-enhance-exercise-performance.
Authorized Officer: Schwald, Claudia, International Search Report issued in PCT application No. PCT/EP2017/063673, Sep. 4, 2017, 3 pp.

* cited by examiner

*Primary Examiner* — Kyung S Chang
(74) *Attorney, Agent, or Firm* — Kaplan Breyer Schwarz, LLP

(57) ABSTRACT

A solubilisation product consists of resveratrol, polysorbate 80 and polysorbate 20, and at least one medium-chain triglyceride.

10 Claims, No Drawings

RESVERATROL SOLUBILITY

FIELD

The invention relates to a resveratrol solubilisation product.

BACKGROUND

Resveratrol is a phytoalexin with antioxidative properties and is a polyphenol. The substance is present, for example, in grapes, in relatively large amounts in the skin of red grapes, but also in raspberries, mulberries, plums, peanuts, and in Japanese knotgrass. Resveratrol can be isolated from grape vines as well. According to the "Wikipedia" online encyclopedia entry, there is some evidence available from in-vitro studies to indicate possible efficacy against cancer cells and beneficial effects in diseases such as atherosclerosis, heart disease, Alzheimer's disease, arthritis, and some autoimmune diseases.

According to a report published in "Pharmazeutische Zeitung Online", issue 29/2007, the anti-oxidative effect of resveratrol is of significance not only for the protection of vessels. As an organ that is particularly rich in lipids, the brain also suffers when exposed to excessive oxidative stress. Accordingly, a neuro-protective effect of resveratrol, which is capable of crossing the blood-brain barrier, was demonstrated in several in-vivo studies in rats. More recent studies even indicate that resveratrol directly promotes the processing of beta-amyloid, which is the pathogenic factor underlying Alzheimer's dementia.

Aside from oxidative stress, chronic low-level inflammation is being discussed as a factor for ageing processes proceeding at an increased rate. According to the report cited above, the intracellular signalling pathway effecting increased production of pro-inflammatory cytokines involves the nuclear factor, kappa-b (NFκ-b). This factor can be activated by a whole range of stimuli (UV radiation, bacterial toxins) and then migrates to the nucleus of the cell, where it induces gene expression of various inflammatory enzymes. NFκ-b is increasingly seen as the crucial switching point linking oxidative and inflammatory processes. Under in-vitro conditions, resveratrol inhibits the nuclear translocation of NFκ-b and thus prevents one of the most important mechanisms in the genesis of pro-inflammatory mediators.

One of the manifold effects of resveratrol is highly specific for this substance. In various organisms, resveratrol has the same life-prolonging effect as sustained calorie restriction (CR). Therefore, it is a member of the CR mimetics.

Likewise, according to Nathan Gray "Resveratrol could enhance exercise performance" (20 Jun. 2012, www.nutraingredients.com/content/view/print/648155) further studies in various organisms indicate that resveratrol has an effect against cancer and diabetes as well as an Alzheimer-protective effect and anti-inflammatory properties and beneficial cardiovascular effects.

However, one issue of known resveratrol formulations is that these show extremely low plasma levels of drug due to absorption and liver metabolism related factors in the body of the patient. It is recognized that micronizing the resveratrol prior to ingestion can improve bioavailability. To increase the circulating drug levels, it is known that to add further components aside from resveratrol to generate carrier systems, such as, for example, emulsions or liposomes, may provide some benefits. Whereas resveratrol is dissolved in a lipophilic phase and is stabilised in the form of droplets in an aqueous environment in emulsions, resveratrol can be retained in a phospholipid layer in liposomes. This can be used to increase the bioavailability as compared to the native form, but formulations of this type, such as liposomes, are mechanically extremely unstable and are not resistant to the milieu predominating in the stomach.

Moreover, for applications in dietary supplements and beverages it is disadvantageous that the known formulations are non-transparent and do not produce a clear aqueous solution.

SUMMARY

It is an object of the invention to provide a sufficiently stable formulation for oral administration. Specifically, it is an object of the invention to generate a formulation for the resveratrol agent, in which the bioavailability of resveratrol is appropriate such that it allows for intake of significantly reduced amounts as compared to the amounts of native resveratrol that need to be taken up. The optimisation of the absorption of resveratrol through an appropriately suitable formulation is one object of the invention in this context. Moreover, it is an object of the invention to attain a stable homogeneous fine distribution of resveratrol in the corresponding end-products, such as food and dietary supplements.

The invention provides a micellar resveratrol formulation on the basis of which a markedly higher bioavailability than with native resveratrol was determined. The invention provides a solubilisation product consisting of resveratrol, a mixture of polysorbate 80 and polysorbate 20 as well as at least one medium-chain triglyceride.

The formulation according to the invention generates micelles that are loaded with resveratrol by means of the solubilisation product.

DETAILED DESCRIPTION

It has been shown, surprisingly, that the use of polysorbate 80 alone or of polysorbate 20 alone does not lead to the desired stable micelles, which remain stable even at the extremely acidic conditions existing in the stomach and thus release the resveratrol to the organism no earlier than via the small intestinal wall. Only the use of the two emulsifying agents in combination with at least one medium-chain triglyceride allowed the inventor to generate a solubilisation product having said stable micelles.

Medium-chain triglycerides (MCTs) are triglycerides containing medium-chain fatty acids. Medium-chain fatty acids include capronic acid, caprylic acid, capric acid, and lauric acid. These are saturated fatty acids, which are present in tropical plant fats such as coconut oil and palm kernel oil. Low fractions of the substances are also present in milk fat. There is no pure MCT oil in nature, but pure MCT oils can be obtained by synthesis. In the scope of the invention, individual MCTs or a mixture of different MCTs can be used as medium-chain triglycerides.

The invention creates the opportunity to implement a resveratrol formulation with a high load of resveratrol in the micelles without the micelles bursting open and releasing the resveratrol as a sediment upon dilution with water.

In the scope of the invention, the content of resveratrol in the solubilisation product according to the invention can be varied up to very high values without destabilising the micelles. The resveratrol content in a preferred embodiment of the solubilisation product is in the range of 3% by weight to 15% by weight, particularly preferably in the range of 5% by weight to 10% by weight, and in particular is 10% by weight.

The amount of the emulsifying agent mixture made up of polysorbate 20 and polysorbate 80 in the solubilisation product according to the invention is in the range of approximately 65% by weight to approximately 95% by weight, in particular in the range of approximately 70% by weight to approximately 92% by weight, particularly preferably the fraction of the emulsifying agent mixture is approximately 71.8% by weight.

In an advantageous refinement, the amount of the at least one medium-chain triglyceride in the solubilisation product is in the range of at least approximately 2% by weight to approximately 8% by weight, in particular in the range of approximately 3% by weight to approximately 5% by weight, whereby the fraction of the at least one medium-chain triglyceride (MCT fraction) preferably is approximately 4.5% by weight.

Surprisingly, it has been found that the loading capacity of the solubilisation product can be increased by adding tocopherol to the solubilisation product as a further component, in particular mixed tocopherol. If tocopherol is used, it has unexpectedly been found advantageous to increase the proportion of the at least one medium-chain triglyceride. When using, for example, 7.5% by weight of tocopherol in the form of mixed tocopherol, an increase in the MCT content from 4.0% by weight to 4.5% by weight leads to a disproportionate increase in the loading capacity with resveratrol from 5% by weight to 10% by weight.

In the context of the invention, the tocopherol content can be varied, and it has been found that an amount in the range up to about 10% by weight is sufficient. In particular, the amount of the tocopherol content in the solubilisation product according to the invention is in the range of approximately 3% by weight to approximately 6% by weight and preferably the tocopherol fraction is approximately 5.25% by weight.

Depending on the specific application field, the solubilisation product can be produced in the scope of the invention using α-tocopherol and/or β-tocopherol and/or γ-tocopherol and/or δ-tocopherol or using a mixed tocopherols consisting of α-tocopherol, β-tocopherol, γ-tocopherol, and δ-tocopherol.

Compared to the use of, for example, α-tocopherol alone, it has been evident that the use of the same amount of mixed tocopherols imparts a greater anti-oxidative potential to the solubilisation product according to the invention.

Chemical lipophilic antioxidants may also be used in the context of the invention, in addition to or as an alternative to tocopherol. For example, butylhydroxyanisole (BHA; E320), butylhydroxytoluene (BHT, E321), gallate (E310 to 312) or rosemary extract with the active ingredients carnosol and carnosic acid (E392) are an option. The specified so-called "E numbers" refer to the list of food additives authorized by the European Union.

Since the micelles are particularly small in the solubilisation product according to the invention, a clear and lastingly transparent product is obtained. The narrow particle size distribution is another contributing factor, since the distribution of the diameters of the micelles at pH 7 and room temperature, i.e. at a temperature in the range of approximately 18° C. to approximately 22° C., ranges only from approximately 1 nm to approximately 25 nm. In particular, on average, approximately 69.45% by volume+/−0.55% by volume of the particles are larger than 3.22 nm+/−0.06 nm, and, on average, approximately 30.55% by volume+/−0.55% by volume of the particles are larger than 12.74 nm+/−1.04 nm.

At pH 1 and a temperature of 37° C., the distribution of the diameters of the micelles ranges from approximately 2 nm to approximately 900 nm. In particular, on average, approximately 60.35% by volume+/−1.25% by volume of the particles are larger than 10.33 nm+/−0.43 nm, and, on average, approximately 31.75% by volume+/−9.15% by volume of the particles are larger than 161.85 nm+/−4.25 nm.

Since the particle sizes are small, the advantageous formation of a clear liquid, in particular for perception by the human eye, is attained.

The micellar particle size distributions characterised above were measured based on the principle of dynamic light scattering using laser light of a wavelength of 780 nm. The particle size measurements were done with the ParticleMetrix NANOFLEX backscatter particle analyser. The measuring principle is based on dynamic light scattering (DLS) in a 180° heterodyne backscatter arrangement. In this geometry, a part of the laser beam is mixed into the scattered light (heterodyne technique). Due to the short light path of 200 micrometers to 300 micrometers in the sample, backscattering is of advantage for absorbing and highly concentrated samples. The heterodyne technique has an amplifying effect on the signal/noise ratio and on the sensitivity of the sub-100 nm-range.

The laser light is coupled into the Y fork of an optical fibre. The laser light that is partially reflected at the sapphire window of the sample chamber and the light scattered backwards by the sample return in the same fibre. The detector in the second branch of the Y fork records the mutually interfering signals. A rapid Fourier transformation analysis decomposes the fluctuating scattered light fractions into a frequency-dependent so-called "power spectrum". Each frequency component is a Brown's diffusion constant and can thus be assigned to a particle size. The Stokes-Einstein formula is used for conversion to a particle size distribution:

$$D = k \frac{T}{3\pi\eta d_p}$$

This equation links the diffusion constant D, Boltzmann constant k, temperature T, dynamic viscosity η of the medium, and diameter $d_P$ of the particles. A temperature sensor is attached in the measuring device close to the sample in the vicinity of the sapphire window.

Each of the samples was diluted once 1:10 with fully deionised water. For this purpose, the solubilisation product was dissolved in water while stirring. It dissolves fully in water producing a clear solution. This solution is stable and transparent. Subsequently, the NANOFLEX was used to run three measurements for a period of 30 seconds and the mean of the measured values was calculated.

In addition, the samples were adjusted to pH 1 and then measured again at 37° at otherwise unchanged conditions. This was to simulate physiological conditions in terms of the gastric passage of the solubilisation product.

The clarity of the solubilisation product can also be made evident by its low turbidity.

The following working hypothesis is used for this purpose: The solubilisation is the better, the clearer an aqueous dilution of a solubilisation product or other formulation of resveratrol is, i.e. at a pH value of 1.1 and a temperature of 37° C. The better the solubilisation, the better is the bioavailability.

This is evident already from the particularly low turbidity of the solubilisation product, which can be understood to be a kind of characteristic parameter for the bioavailability. The turbidity of the solubilisation product according to the invention is less than 50 FNU, measured by scattered light measurement with infrared light according to the provisions of the ISO 7027 standard at a 1:50 dilution of the solubilisation product in water.

The solubilisation product according to the invention retains its low turbidity even after 24 hours of storage at 21° C. and pH 7 and after 1 hour of storage at 37° C. and pH 1.1, i.e. under the storage conditions at room temperature in aqueous dilution and under the conditions during passage through the stomach. Accordingly, it is the current understanding of the inventor that the resveratrol, having passed through the stomach, is still present in the solubilisation product according to the invention in the form of the stable, very small micelles and can therefore be taken up very well in the later digestive tract.

For experimental determination of the turbidity, the turbidity measuring devices are calibrated using a standard suspension. The display therefore does not show the measured light intensity, but the concentration of the calibration suspension. Accordingly, measuring any suspension, the display indicates that the corresponding liquid causes the same light scattering as the standard suspension of the displayed concentration. Formazine is the internationally defined reference standard for turbidity. "FNU", i.e. "formazine nephelometric units", is one of the most common units. This is the unit used, for example, in water treatment for the measurement at 90° C. in accordance with the provisions of the ISO 7072 standard.

In an advantageous embodiment, the solubilisation product of the invention contains at least one other polyphenol, as a further component, in particular quercetin and/or catechin, which can synergistically support the effect of resveratrol, depending on the field of application.

The transparent and fully stable water-soluble resveratrol formulation according to the invention comprises, in the absence of the excipients specified above, stable transparency and, moreover, markedly improved bioavailability in pH-independent manner in gelatine-free capsules (hard and/or soft) and in beverages or liquid, water-based end-products. Products comprising said transparency and water solubility, but also, in particular, this high level of bioavailability of the resveratrol formulation, are urgently sought after in the pertinent industry as capsule filling and as transparent resveratrol beverages for innovative products. A resveratrol formulation meeting these requirements does not yet exist to the knowledge of the inventor.

By means of the specific formulation, the invention managed to markedly increase the bioavailability as compared to the native form of resveratrol.

Due to the markedly increased bioavailability of resveratrol in the solubilisation product according to the invention as compared to the native form, the amount of resveratrol to be taken up daily by a user by oral administration can be reduced. Accordingly, it has been evident, for example, that the administration of 200 mg resveratrol in a solubilisation product according to the invention is sufficient to attain the effect of a daily dose of 3,500 mg native resveratrol.

In principle, the solubilisation product can be used both externally by application to skin, nails, and/or hair or internally by uptake into the body. Use of the solubilisation product is possible in all forms of application, in particular oral, dermal, intravenous or inhalational administration of the solubilisation product or of a fluid containing the solubilisation product.

It has also been evident to be advantageous that the solubilisation product according to the invention can be provided easily in the form of capsules for oral intake, since it does not attack the capsules. Accordingly, the invention also provides a capsule filled with the solubilisation product, whereby the capsule can be provided as soft gelatine capsule or hard gelatine capsule or as soft gelatine-free capsule or as hard gelatine-free capsule.

Another administration form is a fluid containing the solubilisation product according to the invention, and such fluid may be a food, a beverage, a cosmetic product such as in particular a cream, lotion or ointment. Specifically, the fluid can comprise an aqueous dilution of the solubilisation product. The usability in a fluid of the solubilisation product according to the invention is not linked to the viscosity thereof; likewise, the solubilisation product can be incorporated into hydrophilic and lipophilic media.

Due to the increased bioavailability as compared to the native form that can be attained by means of the invention, the daily doses can be markedly reduced in advantageous manner as compared to the oral administration of native resveratrol.

Exemplary embodiments of solubilisation products according to the invention are illustrated hereinafter.

Example 1: Resveratrol Solubilisation Product

For producing a solubilisation product without tocopherol, the following was used:

| | |
|---|---|
| 50 g | resveratrol; |
| 40 g | medium-chain triglycerides; |
| 840 g | polysorbate 80; and |
| 70 g | polysorbate 20. |

The resveratrol used was (trans)resveratrol, 99%, trade name resVIDA, made by Koninklijke DSM N.V., Heerlen, The Netherlands.

MCT oil Delios VK Kosher made by Cognis GmbH, Monheim, Germany, was used as the medium-chain triglycerides.

Crillet 4/Tween 80-LQ-(SG), Croda GmbH, Nettetal, Germany, was used as the polysorbate 80.

Crillet 1/Tween 20-LQ-(SG), Croda GmbH, Nettetal, Germany, was used as the polysorbate 20.

Polysorbate 20 and polysorbate 80 were mixed and heated to a temperature in the range between approximately 50° C. and approximately 70° C.

The MCT oil was added to the mixture of polysorbate 20 and polysorbate 80 at a temperature in the range between approximately 50° C. and approximately 70° C. and homogenized while stirring.

Resveratrol was then added to the mixture of polysorbate 20, polysorbate 80, and MCT oil and heated, while stirring, to a temperature in the range between approximately 83° C. and approximately 87° C. for homogenisation. As soon as the fluid was homogeneous and transparent, it was cooled to a temperature below approximately 60° C.

Example 2: Resveratrol Solubilisation Product with Mixed Tocopherol

For production of the solubilisation product, only

| | |
|---|---|
| 100 g | resveratrol; |
| 45 g | medium-chain triglycerides; |
| 600 g | polysorbate 80; |
| 180 g | polysorbate 20, and |
| 75 g | mixed tocopherols | were used.

The resveratrol was (trans-)resveratrol, 99%, CAS number 501-36-0, procured from Bachem AG, Bubendorf, Switzerland. The CAS number is an international reference standard for chemical substance. Each known chemical substance has a unique CAS number.

MCT oil (70/30) Rofetan GTCC 70/30 made by DHW Deutsche Hydrierwerke Rodleben GmbH, Dessau-Roßlau, Germany, CAS number 73-398-61-5, was used as the medium-chain triglycerides.

Commercial preparations such as, for example, TEGO SMO 80 V, Evonik or Crillet 4/Tween 80-LQ-(SG), Croda GmbH, Nettetal, Germany, can be used as polysorbate 80 (E433, CAS number 9005-65-6).

Commercial preparations such as, for example, TEGO SML 20 V, Evonik or Crillet 1/Tween 20-LQ-(SG), Croda GmbH, Nettetal, Germany, can be used as polysorbate 20 (E432, CAS number 9005-64-5).

Vitapherole T-70 Non GMO, a 70% mixed tocopherols in plant oil made by Vitae Caps S.A., Spain, or EMix 70 made by Nutrilo GmbH, Cuxhaven, Germany, can be used as mixed tocopherols (E306, CAS numbers 59-02-9, 16698-35-4, 54-28-4, and 119-13-1).

Polysorbate 20, polysorbate 80, mixed tocopherols, and MCT oil were homogenised at a temperature in the range of approximately 18° C. to approximately 22° C. while stirring.

Resveratrol was then added to the mixture of polysorbate 20, polysorbate 80, mixed tocopherols, and MCT oil and heated, while stirring, to a temperature in the range of approximately 83° C. to approximately 87° C. for homogenisation. As soon as the fluid was homogeneous and transparent, it was cooled to a temperature below approximately 30° C.

The resulting solubilisation product is a light brown viscous fluid, which produces a yellowish clear solution when diluted with water at a ratio of 1:50. According to an HPLC analysis, the resveratrol content of the solubilisation product is at least 10% by weight, whereby the resveratrol is enclosed in micelles. According to an aerometer measurement, the density of the solubilisation product is in the range of 1.05 to 1.15 g/cm$^3$ at a temperature of 20° C. The turbidity of the solubilisation product is less than or equal to 50 FNU, solution in water at a ratio of 1:50. Said solution has a pH in the range of 6 to 8 according to a potentiometric determination.

It is evident to a person skilled in the art that the invention is not limited to the exemplary embodiments described above, but rather can be varied in manifold ways. Specifically, the features of the individual exemplary embodiments can also be combined with each other or interchanged.

The invention claimed is:

1. A solubilisation product consisting of:
resveratrol;
an emulsifying mixture of polysorbate 80 and polysorbate 20; and
at least one medium-chain triglyceride (MCT).

2. The solubilisation product according to claim 1, characterised in that:
the fractional amount of the resveratrol is in the range of 3% by weight to 15% by weight, or in the range of 5% by weight to 10% by weight, or the fractional amount of the resveratrol is 10% by weight.

3. The solubilisation product according to claim 1, characterised in that:
the fractional amount of the emulsifying agent mixture of polysorbate 20 and polysorbate 80 is in the range of approximately 65% by weight to approximately 95% by weight, or in the range of approximately 70% by weight to approximately 92% by weight or the fractional amount of the emulsifying agent mixture of polysorbate 20 and polysorbate 80 is approximately 71.8% by weight.

4. The solubilisation product according to claim 1, characterised in that:
the fractional amount of the at least one medium-chain triglyceride is in the range of approximately 2% by weight to approximately 8% by weight, or in the range of approximately 3% by weight to approximately 5% by weight, or the fractional amount of the at least one medium-chain triglyceride is approximately 4.5% by weight.

5. The solubilisation product according to claim 1, characterized in that:
the solubilisation product has micelles wherein a distribution of diameters of the micelles ranges from approximately 1 nm to approximately 25 nm.

6. The solubilisation product according to claim 1, characterised in that:
a turbidity of the solubilisation product is less than 50 FNU, measured by scattered light measurement with infrared light according to the provisions of the ISO 7027 standard at a 1:50 dilution of the solubilisation product in water.

7. The solubilisation product according to claim 1, characterised in that:
a turbidity of the solubilisation product after 24 hours of storage at room temperature and pH 7 is less than 50 FNU, measured by scattered light measurement with infrared light according to the provisions of the ISO 7027 standard at a 1:50 dilution of the solubilisation product in water.

8. The solubilisation product according to claim 1, characterised in that:
a turbidity of the solubilisation product after 1 hour of storage at 37° C. and pH 1.1 is less than 50 FNU, measured by scattered light measurement with infrared light according to the provisions of the ISO 7027 standard at a 1:50 dilution of the solubilisation product in water.

9. A solubilisation product consisting of:
resveratrol;
an emulsifying mixture of polysorbate 80 and polysorbate 20;
at least one medium-chain triglyceride (MCT); and
a polyphenol, wherein the polyphenol is quercetin, catechin, or quercetin and catechin.

10. A capsule filled with a solubilisation product according to claim 1,
characterised in that:
the capsule is a soft gelatine capsule, a hard gelatine capsule, a soft gelatin-free capsule, or a hard gelatine-free capsule.

* * * * *